(12) United States Patent
Shin et al.

(10) Patent No.: US 11,953,591 B2
(45) Date of Patent: Apr. 9, 2024

(54) ULTRASOUND IMAGING SYSTEM WITH PIXEL EXTRAPOLATION IMAGE ENHANCEMENT

(71) Applicant: KONINKLIJKE PHILIPS N.V., Eindhoven (NL)

(72) Inventors: Jun Seob Shin, Winchester, MA (US); Francois Guy Gerard Marie Vignon, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 365 days.

(21) Appl. No.: 17/259,311

(22) PCT Filed: Jul. 2, 2019

(86) PCT No.: PCT/EP2019/067651
§ 371 (c)(1),
(2) Date: Jan. 11, 2021

(87) PCT Pub. No.: WO2020/011589
PCT Pub. Date: Jan. 16, 2020

(65) Prior Publication Data
US 2021/0255321 A1    Aug. 19, 2021

Related U.S. Application Data

(60) Provisional application No. 62/696,413, filed on Jul. 11, 2018.

(51) Int. Cl.
*G01S 15/89*     (2006.01)
*A61B 8/00*      (2006.01)
(Continued)

(52) U.S. Cl.
CPC ........ *G01S 15/8906* (2013.01); *A61B 8/5207* (2013.01); *A61B 8/54* (2013.01); *G01S 7/52026* (2013.01); *G01S 7/52077* (2013.01)

(58) Field of Classification Search
CPC ............. G01S 7/52077; G01S 7/52026; A61B 8/5269
See application file for complete search history.

(56) References Cited

U.S. PATENT DOCUMENTS 5,913,824 A * 6/1999 Ogasawara ......... G01S 15/8981
600/455
5,954,653 A * 9/1999 Hatfield .............. G01S 15/8993
600/443
(Continued)

FOREIGN PATENT DOCUMENTS

KR     20120065658 A  *  6/2012
WO  WO-2009130647 A1 * 10/2009 ............. A61B 8/463
WO     2015136534 A1    9/2015

OTHER PUBLICATIONS

F. Sattar et al, "Image Enhancement Based on a Nonlinear Multiscale Method", IEEE Transaction on Imaging Processing, vol. 6, No. 6, pp. 888-895, Jun. 1997 (Year: 1997).*

(Continued)

*Primary Examiner* — Joel Lamprecht
*Assistant Examiner* — Nyrobi Celestine (57) ABSTRACT

An ultrasound imaging system produces images with enhanced resolution or contrast by extrapolation of two ultrasound images of different imaging characteristics, such as aperture size, imaging frequency, or degree of image compounding. In order to prevent the display of image artifacts, extrapolation is accompanied by artifact removal and image smoothing.

16 Claims, 4 Drawing Sheets

(51) Int. Cl.
    *A61B 8/08* (2006.01)
    *G01S 7/52* (2006.01)

(56) References Cited

U.S. PATENT DOCUMENTS

| | | | | |
|---|---|---|---|---|
| 6,454,714 | B1* | 9/2002 | Ng | G01S 7/52039 600/443 |
| 2005/0053305 | A1* | 3/2005 | Li | A61B 8/00 382/260 |
| 2006/0233455 | A1 | 10/2006 | Cheng et al. | |
| 2007/0285421 | A1* | 12/2007 | Kobayashi | A61B 8/00 345/424 |
| 2008/0068014 | A1* | 3/2008 | Dannels | G01R 33/561 702/57 |
| 2008/0208061 | A1* | 8/2008 | Halmann | G01S 15/8995 600/459 |
| 2009/0253986 | A1* | 10/2009 | Frinking | G01S 7/52074 600/431 |
| 2009/0306503 | A1* | 12/2009 | Srinivasan | A61B 8/461 600/441 |
| 2009/0306513 | A1* | 12/2009 | Srinivasan | A61B 8/06 600/454 |
| 2010/0041993 | A1* | 2/2010 | Osumi | A61B 8/08 600/443 |
| 2011/0054317 | A1* | 3/2011 | Lin | G01S 7/52033 600/443 |
| 2012/0108974 | A1* | 5/2012 | Katou | A61B 8/467 600/445 |
| 2012/0226159 | A1 | 9/2012 | Sinclair et al. | |
| 2013/0016092 | A1* | 1/2013 | Collins | A61B 8/466 345/419 |
| 2013/0204135 | A1* | 8/2013 | Kucewicz | G06T 5/00 600/443 |
| 2013/0343627 | A1* | 12/2013 | Zwirn | A61B 8/5269 382/131 |
| 2015/0148678 | A1* | 5/2015 | Hashiba | G01S 15/8959 600/447 |
| 2015/0196279 | A1* | 7/2015 | Ketterling | A61B 8/145 600/447 |
| 2015/0359507 | A1* | 12/2015 | Shibata | A61B 8/488 600/443 |
| 2016/0128675 | A1 | 5/2016 | Kang et al. | |
| 2017/0143313 | A1* | 5/2017 | Pelissier | A61B 8/565 |

OTHER PUBLICATIONS

A. Achim et al, "Novel Bayesian Multiscale Method for Speckle Removal in Medical Ultrasound Images", IEEE Transaction on Medical Imaging, vol. 20, No. 8, pp. 772-783, Aug. 2001 (Year: 2001).*

A. Sappa et al, "Wavelet-Based Visible and Infrared Image Fusion: A Comparative Study", Sensors, vol. 16, No. 861, Jun. 2016 (Year: 2016).*

Sonam et al, "Discrete Wavelet Transform and Cross Bilateral Filter based Image Fusion", I.J. Intelligent Systems and Applications, pp. 37-45, vol. 1, Jan. 2017 (Year: 2017).*

KR-20120065658-A (Year: 2012).*

Carotenuto, et al., "A New Extrapolation Technique for Resolution Enhancement of Pulse-Echo Imaging Systems", IEEE Transactions on Ultrasonics, Ferroelectrics, and Frequency Control, vol. 49, No. 3, Mar. 2002, pp. 374-382.

International Search Report and Written Opinion for International Application No. PCT/EP2019/067651, filed Jul. 2, 2019, 16 pages.

Swingler, et al., "Line-Array Beamforming Using Linear Prediction for Aperture Interpolation and Extrapolation", IEEE Transactions on Acoustics, Speech, and Signal Processing, vol. 37, No. 1, Jan. 1989, pp. 16-30.

Xu, et al., "An improved extrapolation method and its application in ultrasound computerized tomography", ScienceDirect, Procedia Engineering, Jul. 2010, pp. 335-341.

* cited by examiner

ULTRASOUND IMAGING SYSTEM WITH PIXEL EXTRAPOLATION IMAGE ENHANCEMENT

RELATED APPLICATION

This application is the U.S. National Phase application under 35 U.S.C. § 371 of International Application No. PCT/EP219/067651, filed on Jul. 2, 2019, which claims the benefit of and priority to U.S. Provisional No. 62/696,413, filed Jul. 11, 2018, which is incorporated by referenced in tis entirety.

TECHNICAL FIELD

This invention relates to ultrasound imaging systems and, in particular, to ultrasound imaging systems which use extrapolation processing of image values to enhance image resolution or contrast.

BACKGROUND

In ultrasound imaging, the image characteristics including the spatial resolution, contrast resolution, frame rate, and tissue uniformity are closely linked. This means that at least one of these characteristics needs to be compromised in order to achieve an improvement in another characteristic. For example, a higher imaging frequency can achieve better spatial resolution but at the expense of reduced penetration depth. A larger aperture can achieve better lateral resolution but at the expense of increased system complexity and cost. Plane wave and diverging wave imaging can achieve significantly enhanced frame rates by imaging the whole medium with as little as just one transmit firing. However, this is achieved at the expense of reduced image contrast and generally also requires an ultrasound system that can support high-order multilines and their beam formation.

One technique that has been proposed to overcome these limitations and inherent conflicts is the extrapolation of images of different characteristics to estimate image values which are an enhancement of the extrapolated images. See, for instance, "A New Extrapolation Technique for Resolution Enhancement of Pulse-Echo Imaging Systems," by Crotenuto et al., *IEEE Trans. Ult., Ferroelec., and Freq. Control.*, vol. 49, no. 3 (March 2002). This paper proposes to extrapolate the pixel values of two images of different aperture sizes (i.e., different numbers of transducer elements) to produce a resultant image with improved resolution. However, the described technique is subject to the production of images with undesired artifacts, and can produce images with unintended enhancement of the speckle artifacts inherent in coherent imaging modalities such as ultrasound.

SUMMARY

Systems and methods of the invention provide image improvement through extrapolation without the creation of new image artifacts, and which takes into consideration the speckle artifacts characteristic of ultrasound imaging.

In accordance with the principles of the present invention, the resolution or contrast of an ultrasound image is improved by extrapolation of two ultrasound images of different imaging characteristics, such as aperture size, imaging frequency, or degree of image compounding. In order to prevent the display of image artifacts, extrapolation is accompanied by artifact removal and image smoothing.

In certain aspects, systems for producing extrapolated images include a transducer array probe; and one or more processors in communication with the transducer array probe. The one or more processors are configured to perform one or more of the following steps: separate signals received by the transducer array probe into two imaging signal paths of different imaging characteristics; beamform signals, from each imaging signal path, for images of different imaging characteristics; produce ultrasound images of different imaging characteristics; predict an image by extrapolation of the ultrasound images; remove artifacts from extrapolated images; perform smoothing of the speckle of extrapolated images; and display a final image predicted by extrapolation.

In further aspects, systems for producing extrapolated images include a transducer array probe, a signal separator, adapted to separate signals received by the transducer array probe into two imaging signal paths of different imaging characteristics; a beamformer coupled to the signal separator in each imaging signal path which is adapted to beamform signals for images of different imaging characteristics; an image processor coupled to the beamformer in each imaging signal path and configured to produce ultrasound images of different imaging characteristics; an extrapolator coupled to the image processor and adapted to predict an image by extrapolation of the ultrasound images; an artifact filter coupled to the extrapolator and adapted to remove artifacts from extrapolated images; a speckle filter coupled to the artifact filter and adapted to perform smoothing of the speckle of extrapolated images; and a display, coupled to the speckle filter, and adapted to display a final image predicted by extrapolation, It is understood that one or more processors may used to execute the processes of, e.g., the beamformer, extrapolator, artifact filter, speckle filter, and signal separator.

Figure 1:
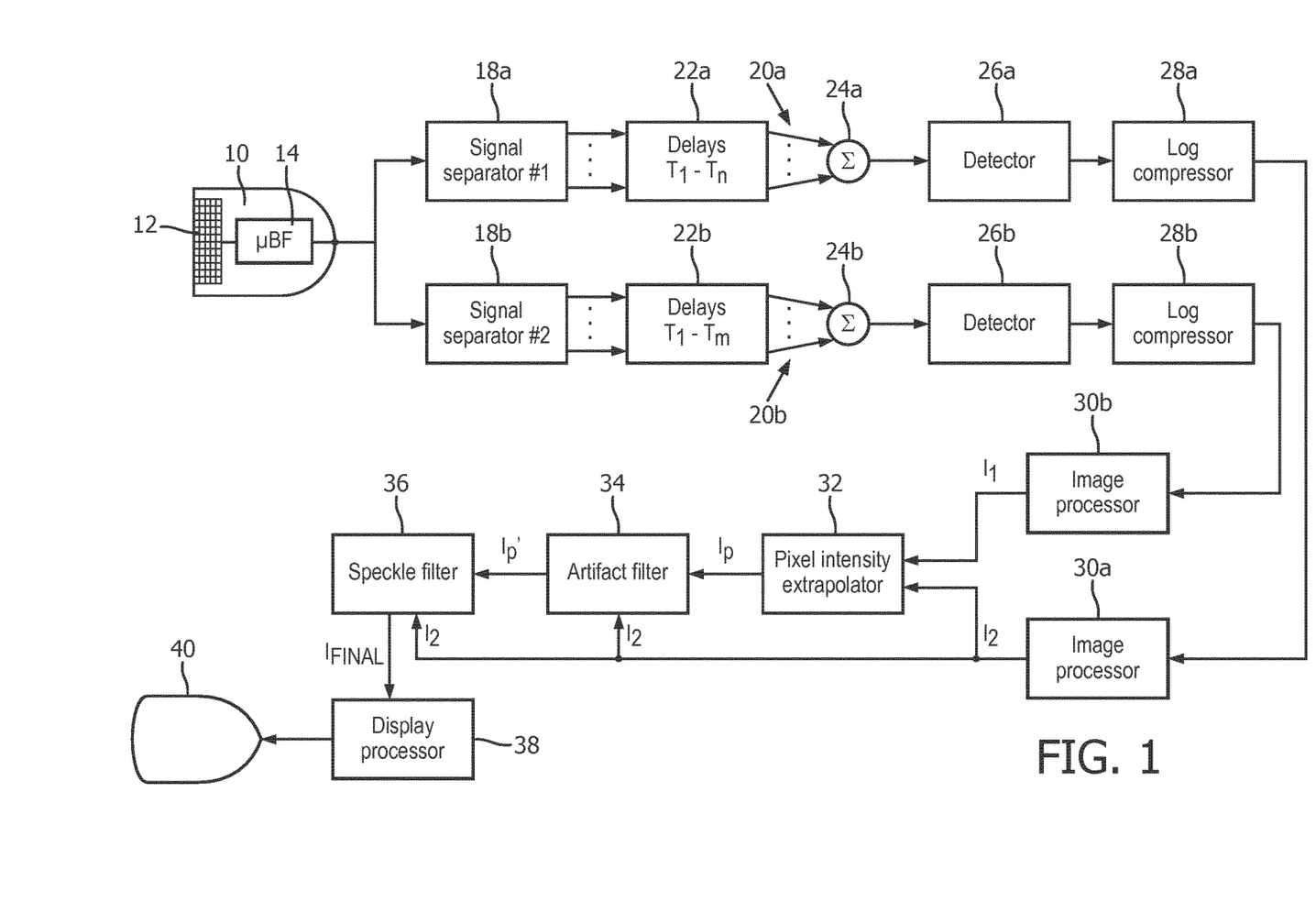
FIG. 1 illustrates in block diagram form an ultrasound system configured in accordance with the principles of the present invention.

Referring first to FIG. 1, an ultrasonic imaging system constructed in accordance with the principles of the present invention is shown in block diagram form. A transducer array 12 is provided in an ultrasound probe 10 for transmitting ultrasonic waves and receiving echo information. The transducer array 12 may be a one- or two-dimensional array of transducer elements capable of scanning in two or three dimensions, for instance, in both elevation (in 3D) and azimuth. The transducer array 12 is coupled to an optional microbeamformer 14 in the probe which controls transmission and reception of signals by the array elements. Among the transmit characteristics controlled by the microbeamformer when so equipped, or a separate transmit beamformer (not shown) used by 1D arrays, are the number, direction, spacing, amplitude, phase, frequency, polarity, and diversity of transmit waveforms. Beams formed in the direction of pulse transmission may be steered straight ahead from the transducer array, or at different angles on either side of an unsteered beam for a wider sector field of view. For some applications, unfocused plane waves may be used for transmission. Another imaging technique is to transmit and receive echoes from diverging transmit waves. Most 1D array probes of relatively small array length, e.g., a 128-element array, do not use a microbeamformer but are driven from and respond directly to a main system beamformer. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.)

Figure 2A:
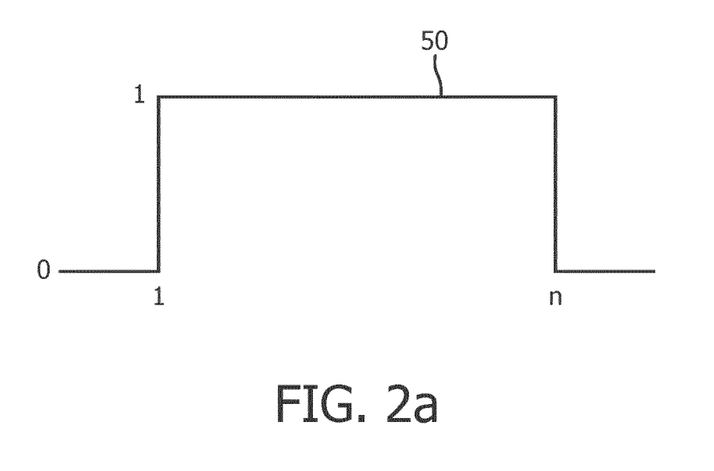
FIGS. 2a and 2b illustrate two apodization functions suitable for producing images of different aperture sizes.
Figure 2B:
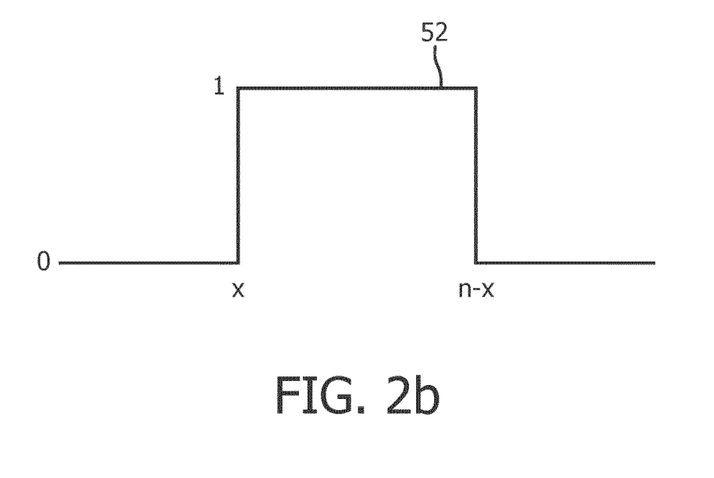

In the system of FIG. 1, the probe 10 is coupled to two signal separator circuits, signal separator #1 and signal separator #2. The signal separators cause the echo signals received by the probe 10 to be processed in different ways, producing two images of different imaging characteristics. For instance, the signal separators can comprise apodization circuits which apply different apodization weighting to the echo signals received from elements of the array 12, as illustrated by FIGS. 2a and 2b. FIG. 2a illustrates an apodization function 50 for an array of n transducer elements; "n" may be 64 elements, for example. The apodization function 50 weights the full aperture, all of the n elements, with a weight of one. The apodization function 52 of FIG. 2b produces a smaller aperture of the signals from the n transducer elements. As function 52 illustrates, the first "x" elements of the full aperture and the last "x" elements of the full aperture have weights of zero; the central elements have a weight of one. For example, function 50 would provide a set of signals from a full 64-element aperture and, if x is equal to eight, then function 52 would provide a set of signals from the central 48 elements of the array. The signals passed by these different apodization functions are then used to produce two different images, one from a 64-element aperture and the other from a 48-element aperture.

Figure 3A:
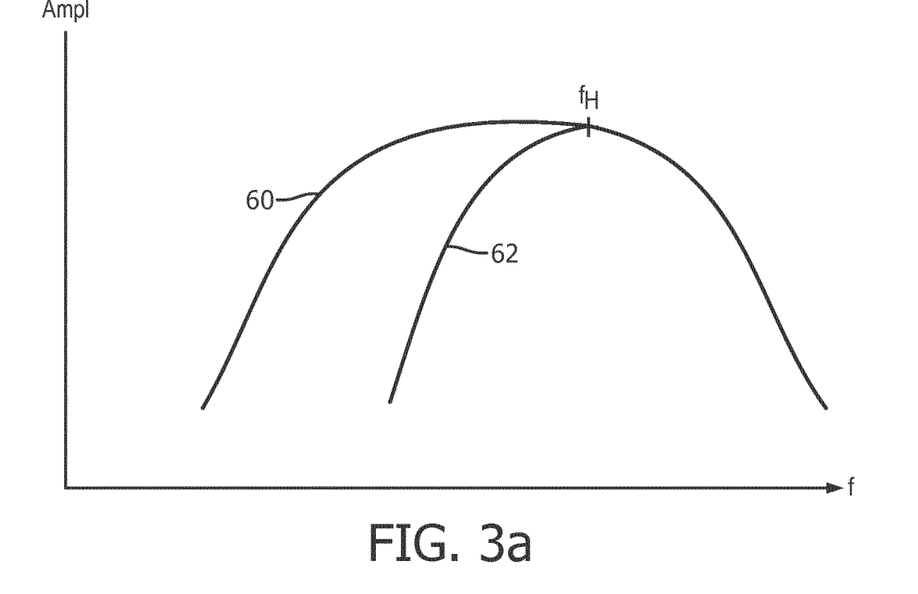
FIGS. 3a and 3b illustrate two filter characteristics suitable for producing images of different imaging frequencies.
Figure 3B:
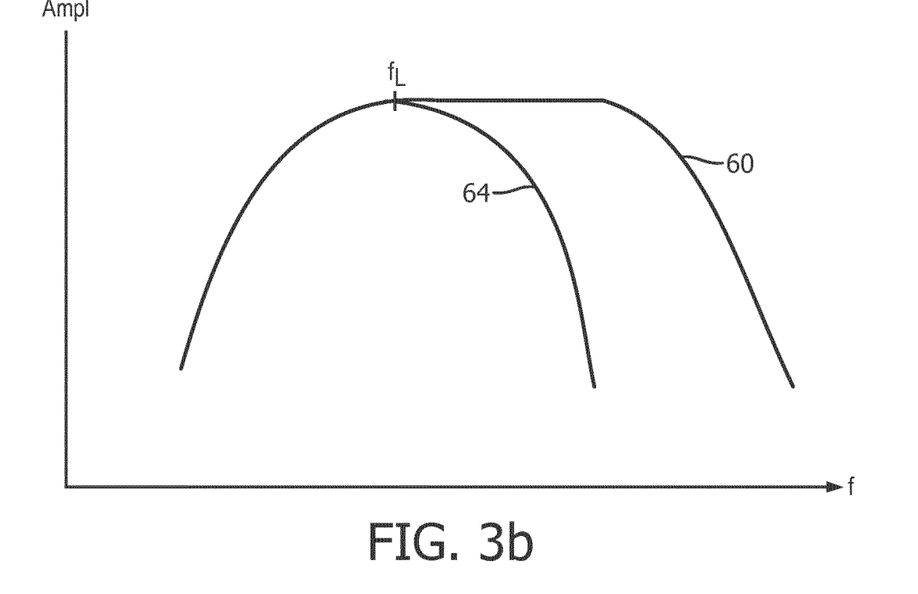

FIGS. 3a and 3b illustrate another form which the signal separators may take, which is to provide sets of signals of different frequencies for imaging. In these drawings the curve 60 represents the full frequency band of the transducer elements. In FIG. 3a only the upper portion of the full frequency band is passed by one of the signal separators as shown by curve 62 centered at a high frequency $f_H$. In FIG. 3b only the lower portion of the full frequency band is passed by the other signal separator, as shown by curve 64 in the drawing. Thus, the two signal separators when functioning as a high pass and a low pass filter would lead to the production of a high frequency image and a low frequency image. Another way to differentiate the frequencies of the two images would be to allow one signal separator to pass the full bandwidth 60 of signal frequencies, and restrict the other signal separator to pass only a limited central portion of the full band, thus leading to the production of a wide bandwidth image and a narrow bandwidth image.

The sets of echo signals passed by the two signal separators 18a and 18b are beamformed in parallel by appropriately delaying them and then combining them in beamformers 20a and 20b. The partially beamformed signals produced by the microbeamformer 14 from each patch are coupled to the beamformers 20a and 20b where partially beamformed signals from individual patches of transducer elements are combined into a fully beamformed coherent echo signal, or echo signals from elements of a one-dimensional array without a microbeamformer are delayed and combined. Each beamformer comprises delays 22a and 22b coupled to summers 24a and 24b. In the case of the apodized signals produced by apodization functions 50 and 52, the signals from the full aperture would be appropriately delayed by the n delays of 22a then coherently summed in 24a, and the m delays of 22b would delay the signals of the narrower aperture x through n–x, with m equal to n–2x. The m delayed echo signals are then coherently summed in 24b. In the case of frequency differentiation as illustrated in FIGS. 3a and 3b, m and n would be equal, since it is frequency, not aperture size, which is the differentiating imaging characteristic.

The coherent echo signals of the two imaging signal paths may then undergo signal processing such as noise filtering or noise reduction as by spatial or frequency compounding. The echo signals in the two signal paths are then detected by detectors 26a and 26b, which may function as amplitude (envelope) detectors. The detected imaging signals are then log compressed by log compressors 28a and 28b, which may be constructed as look-up tables that convert the signal values to a more diagnostic logarithmic range of display values. The signals of the two paths are then formed into respective images by image processors 30b and 30a. The image processors may comprise scan converters and image memories which arrange the received signals in a desired display format such as a sector or rectangular form, then stores them for further processing.

In accordance with the principles of the present invention, the images produced by the image processors 30b and 30a are processed by a pixel intensity extrapolator 32 to extrapolate an enhanced image. Following on the previous example, the extrapolator 32 can process an image produced by 48 transducer elements with one produced by 64 transducer elements to predict image values that would be produced by a 128-element array. Image $I_1$, that produced by 48 transducer elements, and image $I_2$, which is produced by 64 transducer elements and thus should be a better image, are used to produce an image $I_p$, an image predicted to be produced by an even greater number of transducer elements. An image produced by an $N_1$ number of elements is used with one produced by an $N_2$ number of elements to predict values for an image from $N_p$ elements, where $N_1 < N_2 < N_p$. Similarly, an image obtained with an imaging frequency of $f_1$ and another image obtained with an imaging frequency of $f_2$, can be used to predict what an image at an imaging frequency of $f_p$ would look like where $f_1 < f_2 < f_p$. In the case of plane wave imaging and divergent wave imaging, if $N_2$ plane/diverging waves are used, it is possible to form an image with $N_1$ plane/diverging waves coherently compounded and another image with $N_2$ plane/diverging waves coherently compounded and predict what an image with $N_p$ plane/diverging waves coherently compounded would look like, where $N_1 < N_2 < N_p$.

The extrapolator 32 can operate to perform linear or nonlinear (quadratic) extrapolations. The extrapolator 32 can operate to produce a two-dimensional predicted image in x and y image coordinates by processing the image values of images $I_1$ and $I_2$ with the equation $$I_p(x, y) = I_1(x, y) + \frac{I_2(x, y) - I_1(x, y)}{N_2 - N_1}(N_p - N_2)$$

where $I_1(x, y)$ and $I_2(x, y)$ are the two images obtained with parameters $N_1$ and $N_2$, respectively. The parameters $N_1$ and $N_2$ can represent the number of elements in the aperture (aperture size), the imaging frequency or the number of plane or diverging waves coherently compounded, depending on the specific differentiating characteristic for which the equation is used.

Any extrapolation technique simply attempts to make a prediction based on the trend that is observed with the available data of the input images. A characteristic of ultrasound which is not susceptible to accurate prediction by extrapolation is image speckle caused by the coherent nature of the acoustic signals. Due to the random nature of speckle, the trend in the speckle region is often not reliable enough to be used to predict subsequent, improved images, particularly when a simple extrapolation scheme is used. Therefore, image artifacts in the speckle region are inevitable especially if $N_p$ is much greater than $N_1$ and $N_2$.

To avoid such image artifacts and increase the robustness of the technique, a few additional steps are necessary. An artifact-free image $I_{p'}$ is obtained by taking the minimum of the two images $I_2(x, y)$ and the predicted image $I_p(x, y)$ on a pixel-by-pixel basis and then forcing any negative values to zero. An artifact filter 34 performs this operation in the system of FIG. 1 by executing the equation $$I_{p'}(x,y)=\max[\min\{I_2(x,y),I_p(x,y)\},0]$$

This corrects any pixel intensity values that become clipped or go out of the grayscale range of the image values (e.g., zero to 255) as a result of erroneous prediction while ensuring that the image quality is never degraded from the reference image $I_2(x, y)$. The $I_2$ image is the image of the best image quality initially available. This is because its imaging parameter $N_2$ is better than that of $I_1$, giving the beams of the $I_2$ image lower sidelobes than those of $I_1$: the better image exhibits a narrower point spread function. The reduced sidelobes capture less undesirable off-axis acoustic energy than the greater sidelobes of $I_1$, and as a result the $I_2$ image signals will be less bright (lower in amplitude) than those of $I_1$. If an $I_p$ image value is of even greater quality than an $I_2$ image value, it would exhibit an even lower signal level due to even lower sidelobes and be selected for $I_{p'}$ by the min operator, but if not, the $I_2$ image value is selected for $I_{p'}$ by the preceding equation. The max operator avoids the inclusion of out-of-range negative image values.

A speckle filter 36 then produces the value for a display image $I_{FINAL}$ using the values of $I_2$ and $I_{p'}$. The speckle filter 36 provides a smoothing of image speckle so that any changes in the speckle variance and image brightness due to extrapolation are adjusted to match the original image without compromising the benefits from the extrapolation technique. A suitable speckle filter for producing a final image with improved resolution that is extrapolated from images of different aperture sizes is $$I_{Final}=LPF(I_2)+D_{p'}$$

where $I_2$ is the better of the two original images; $I_{p'}$ is the artifact-free, predicted image produced by the artifact filter 34; and $D_{p'}$ is a "Detail" image which contains most of the speckle content of $I_{p'}$. $D_{p'}$ is produced by taking the difference of $$D_{p'}=I_{p'}-LPF(I_{p'})$$

$LPF(I_{p'})$ is an "approximation" image computed as a spatially low pass filtered form of image $I_{p'}$. A simple spatial low pass filter suitable for use in an implementation of the present invention is illustrated conceptually in FIG. 4. This illustration represents a nine-element kernel 70 for spatially processing nine contiguous image elements of an input image I. An image value for an approximation image A is calculated at the central location $I_A$ of the kernel by weighting and summing the eight surrounding image values and the central image value of the input image $I_{p'}$. Mathematically, this process can be expressed as $$I_A = \sum_{n=1}^{9} \frac{1}{9} I_n$$

Figure 4:
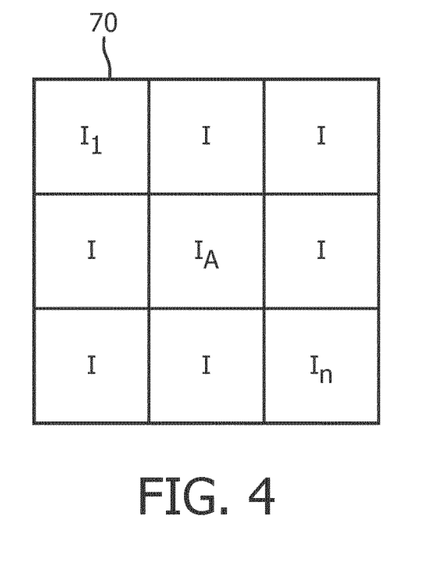
FIG. 4 illustrates a nine-element kernel which may be used to produce a spatially filtered image in accordance with the present invention.

That is, each of the nine image elements of the kernel are weighted by ⅑ and the weighted values of the kernel are then summed to calculate an approximation image value of $I_{p'}$. An approximation image of such values thus will contain primarily low spatial frequency structural information of an image. While this simple example only operates on a small local image area of nine image elements, a preferred kernel size will usually be significantly larger, preferably large enough to encompass input image elements containing a wide (and preferably the full) range of speckle values. Thus, the speckle range can be contained in image "detail" values $D_{p'}$, which can be computed as the difference between the input image $I_{p'}$ and the approximation image $LPF(I_{p'})$ for each image element location.

In a similar manner, the $I_2$ image is decomposed into a spatially low pass filtered approximation image $LPF(I_2)$ from which the speckle detail of the $I_2$ image is absent, since $$D_2=I_2-LPF(I_2)$$

Thus, the speckle filter uses spatial low pass filtering to decompose both the $I_2$ image and the $I_{p'}$ image into an approximation image containing major structural information and a detail image containing image speckle detail. Terms of the decomposed images are then used to produce the final image $I_{FINAL}$ for display.

In summary, the operation of the speckle filter 36 is to first decompose both the original reference image $I_2$ and the artifact-free, predicted image $I_{p'}$ into their respective low-resolution and detail components and then to reconstruct the final image by combining the low-resolution approximation image component of $I_2$ and the detail component of $I_{p'}$. This way, it is possible to benefit from the enhanced resolution in $I_{p'}$ while preserving the smoothness from $I_2$. The final image $I_{FINAL}$ produced by the speckle filter is coupled to a display processor 38 for display on an image display 40.

The above-described operation of the speckle filter 36, as previously mentioned, produces final images extrapolated from input images of different aperture sizes with enhanced lateral image resolution. In the case of frequency-differentiated input images and coherently-compounded plane/diverging wave images differentiated in the degree of compounding, the goal is to achieve improved image contrast rather than improved lateral resolution. The improved contrast of the $I_{p'}$ image is contained in its low spatial frequency component and hence the equation executed by the speckle filter 36 is $$I_{FINAL}=LPF(I_{p'})+D_2$$

which uses the decomposed approximation image $LPF(I_{p'})$ of the $I_{p'}$ image and the speckle detail of the $I_2$ image.

The present inventors have found that the predictions of extrapolated images are increasingly inaccurate when large increments of the differentiating image attributes N are used. Extrapolated images of better quality are produced when an incremental approach to a final extrapolated image is used. For example, suppose the starting images are differentiated in aperture size, with $I_1$ with $N_1$=40 elements and $I_2$ with $N_2$=48 elements. These starting images could be used to directly extrapolate an image with $N_3$=128 elements. However, the accuracy of prediction directly to a 128-element aperture may be low. Instead, the extrapolation process shown in FIG. 1 is applied at small intervals iteratively. For example, $I_1$ with $N_1=40$ elements and $I_2$ with $N_2=48$ elements can be used to obtain $I_3$ with $N_3=56$ elements. Then $I_2$ and $I_3$ can be used to obtain $I_4$ with $N_4=64$ elements, and so on until we obtain $I_p$ with $N_p=128$ elements. Using this smaller incremental approach, new images are predicted at small increments intermediate the starting and final image attributes so that the prediction accuracy is improved and hence artifacts are reduced. The predicted images $I_3 \ldots I_p$ can also be averaged to further enhance the robustness of the technique.

Other variations of the inventive extrapolation technique described above will readily occur to those skilled in the art. For instance, another way to extrapolate images and avoid artifacts in the process is to extrapolate only speckle-free starting images. As seen from the above, the approximation images produced by low pass spatial filtering have much of the speckle detail removed, and can be used for this purpose. A filter which has been found to be especially effective at removing the speckle content of ultrasound images is a Lee filter, which employs selective spatial low pass filtering dictated by the local speckle variance. If the speckle variance over a local region of pixels to be filtered is high, it is presumed that a tissue or blood pool edge is present in the region and filtering is not performed. But if the speckle variance of the region is low, it is presumed that the region consists of a homogeneous area of speckle-contaminated tissue and filtering is performed. After the starting images are spatially filtered by a Lee filter to substantially remove speckle detail, the starting images with speckle removed are used to extrapolate a predicted image. The speckle detail $D_2$ is added to the predicted image at the conclusion of the extrapolation process.

It should be noted that an ultrasound system suitable for use in an implementation of the present invention, and in particular the component structure of the ultrasound system of FIG. 1, may be implemented in hardware, software or a combination thereof. The various embodiments and/or components of an ultrasound system, or components and controllers therein, also may be implemented as part of one or more computers or microprocessors. The computer or processor may include a computing device, an input device, a display unit and an interface, for example, for accessing the internet. The computer or processor may include a microprocessor. The microprocessor may be connected to a communication bus, for example, to access a PACS system or the data network for importing training images. The computer or processor may also include a memory. The memory devices such as ones contained in the image processors 30a and 30b may include Random Access Memory (RAM) and Read Only Memory (ROM). The computer or processor further may include a storage device, which may be a hard disk drive or a removable storage drive such as a floppy disk drive, optical disk drive, solid-state thumb drive, and the like. The storage device may also be other similar means for loading computer programs or other instructions into the computer or processor.

As used herein, the term "computer" or "module" or "processor" or "workstation" may include any processor-based or microprocessor-based system including systems using microcontrollers, reduced instruction set computers (RISC), ASICs, logic circuits, and any other circuit or processor capable of executing the functions and equations described herein. The above examples are exemplary only, and are thus not intended to limit in any way the definition and/or meaning of these terms.

The computer or processor executes a set of instructions that are stored in one or more storage elements, in order to process input data. The storage elements may also store data or other information as desired or needed. The storage element may be in the form of an information source or a physical memory element within a processing machine.

The set of instructions of an ultrasound system including those controlling the acquisition, processing, and display of ultrasound images as described above may include various commands that instruct a computer or processor as a processing machine to perform specific operations such as the methods and processes of the various embodiments of the invention. The set of instructions, particularly those executing the equations set forth above for the pixel intensity extrapolator, the artifact filter, and the speckle filter, may be in the form of a software program. The software may be in various forms such as system software or application software and which may be embodied as a tangible and non-transitory computer readable medium. Further, the software may be in the form of a collection of separate programs or modules such as a transmit control module, a program module within a larger program or a portion of a program module. The software also may include modular programming in the form of object-oriented programming. The processing of input data by the processing machine may be in response to operator commands, or in response to results of previous processing, or in response to a request made by another processing machine.

Furthermore, the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound imaging system which produces extrapolated images comprising:
   a transducer array probe; and
   one or more processors in communication with the transducer array probe, the processor configured to:
   separate signals received by the transducer array probe into two imaging signal paths of different imaging characteristics;
   beamform signals, from each imaging signal path, for images of different imaging characteristics;
   produce ultrasound images of different imaging characteristics;
   predict an extrapolated image by extrapolation of the ultrasound images;
   remove artifacts resulting from extrapolation which are not speckle from the extrapolated image;
   perform smoothing of the speckle of the extrapolated image; and
   display a final image predicted by the extrapolation.

2. An ultrasound imaging system which produces extrapolated images comprising:
   a transducer array probe;
   a signal separator, adapted to separate signals received by the transducer array probe into two imaging signal paths of different imaging characteristics;
   a beamformer coupled to the signal separator in each imaging signal path which is adapted to beamform signals for images of different imaging characteristics;
   an image processor coupled to the beamformer in each imaging signal path and configured to produce ultrasound images of different imaging characteristics;
   an extrapolator coupled to the image processor and adapted to predict an extrapolated image by extrapolation of the ultrasound images;

an artifact filter coupled to the extrapolator and adapted to remove non-speckle artifacts resulting from extrapolation from the extrapolated image;

a speckle filter coupled to the artifact filter and adapted to perform smoothing of the speckle of the extrapolated image; and a display, coupled to the speckle filter, and adapted to display a final image predicted by the extrapolation.

3. The ultrasound imaging system of claim 2, wherein the extrapolator is further adapted to predict the extrapolated image by extrapolation of ultrasound images differentiated by one or more of aperture size, imaging frequency, or degree of plane wave or diverging wave compounding.

4. The ultrasound imaging system of claim 2, wherein the imaging signal paths each further comprises a detector and a log compressor.

5. The ultrasound imaging system of claim 2, wherein the signal separator further comprises first and second signal separators adapted to separate echo signals received by the transducer array probe into first and second sets of echo signals of different imaging characteristics.

6. The ultrasound imaging system of claim 5, wherein the signal separators further comprise apodization circuits adapted to apply different apodization functions to received echo signals.

7. The ultrasound imaging system of claim 6, wherein the apodization functions are adapted to provide signals from different numbers of transducer elements for images of different aperture sizes.

8. The ultrasound imaging system of claim 5, wherein the signal separators further comprise a high pass filter and a low pass filter adapted to provide signals of different imaging frequencies.

9. The ultrasound imaging system of claim 5, wherein the signal separators further comprise a wide bandpass pass filter and a narrow bandpass filter adapted to provide signals of different imaging frequencies.

10. The ultrasound imaging system of claim 2, wherein the artifact filter is further adapted to produce a predicted extrapolated image by taking the minimum of:

values of the extrapolated image, and values of one of the ultrasound images used to produce the extrapolated image.

11. The ultrasound imaging system of claim 10, wherein the artifact filter is further adapted to avoid the inclusion of out-of-range signals in the displayed final image.

12. An ultrasound imaging system which produces extrapolated images comprising:

a transducer array probe;

a signal separator, adapted to separate signals received by the transducer array probe into two imaging signal paths of different imaging characteristics;

a beamformer coupled to the signal separator in each imaging signal path which is adapted to beamform signals for images of different imaging characteristics;

an image processor coupled to the beamformer in each imaging signal path and configured to produce ultrasound images of different imaging characteristics;

an extrapolator coupled to the image processor and adapted to predict an extrapolated image by extrapolation of the ultrasound images;

an artifact filter coupled to the extrapolator and adapted to remove non-speckle artifacts resulting from extrapolation from the extrapolated image;

a speckle filter coupled to the artifact filter and adapted to perform smoothing of the speckle of the extrapolated image; and a display, coupled to the speckle filter, and adapted to display a final image predicted by the extrapolation, wherein the speckle filter is further adapted to decompose the extrapolated image and an image used by the extrapolator to produce the extrapolated image into a low-resolution image and a detail image containing speckle by spatial low pass filtering.

13. The ultrasound imaging system of claim 12, wherein the speckle filter is further adapted to produce:

a final image containing a low-resolution image component of an image used by the extrapolator to predict an image by extrapolation, and image detail from the image predicted by extrapolation.

14. The ultrasound imaging system of claim 12, wherein the speckle filter is further adapted to produce:

a final image containing a low-resolution image component of an image predicted by extrapolation, and image detail from an image used by the extrapolator to produce the image predicted by extrapolation.

15. The ultrasound imaging system of claim 2, wherein the extrapolator is further adapted to predict an intermediate predicted image by extrapolation of starting ultrasound images, and to predict a final predicted image by extrapolation using at least one intermediate predicted image.

16. The ultrasound imaging system of claim 2, wherein the extrapolator is further adapted to extrapolate two images of different imaging characteristics from which speckle characteristic has been removed.

\* \* \* \* \*